United States Patent
Kitajima et al.

(10) Patent No.: US 6,220,453 B1
(45) Date of Patent: Apr. 24, 2001

(54) BLOOD FILTER UNIT

(75) Inventors: Masao Kitajima; Sigeru Tezuka; Yasuo Washizawa; Kenichiro Yazawa, all of Saitama (JP)

(73) Assignee: Fuji Photo Film Co., Ltd., Kanagawa (JP)

( * ) Notice: Subject to any disclaimer, the term of this patent is extended or adjusted under 35 U.S.C. 154(b) by 0 days.

(21) Appl. No.: 09/287,425

(22) Filed: Apr. 7, 1999

(30) Foreign Application Priority Data

Apr. 7, 1998 (JP) ................................................. 10-093786
Apr. 7, 1998 (JP) ................................................. 10-093787
Apr. 7, 1998 (JP) ................................................. 10-093788

(51) Int. Cl.[7] ............................. B01D 35/00; B01D 33/00
(52) U.S. Cl. ...................... 210/406; 210/416.1; 210/455; 210/473; 210/489; 210/456
(58) Field of Search ................................. 210/416.1, 406, 210/455, 473, 483, 489, 456, 645, 789; 422/101

(56) References Cited

U.S. PATENT DOCUMENTS

| 3,800,947 | * | 4/1974 | Smith | 210/117 |
| 4,202,769 | * | 5/1980 | Greenspan | 210/83 |
| 4,898,572 | * | 2/1990 | Sugugue Nee Lasnier | 604/4 |
| 5,868,928 | * | 2/1999 | Bradley | 210/257.2 |
| 5,979,669 | * | 11/1999 | Kitajima et al. | 210/455 |
| 5,996,811 | * | 12/1999 | Kitajima et al. | 210/488 |

* cited by examiner

Primary Examiner—Chester T. Barry
(74) Attorney, Agent, or Firm—Reed Smith LLP

(57) ABSTRACT

This invention provides a blood filter unit capable of obtaining a necessary volume of a plasma or serum sample from blood to be assayed easily at any place, which comprises a blood filtering material and a holder accommodating the blood filtering material and having a nozzle for sucking blood and a filtrate outlet, and the inside of the holder being kept reduced pressure conditions.

12 Claims, 9 Drawing Sheets

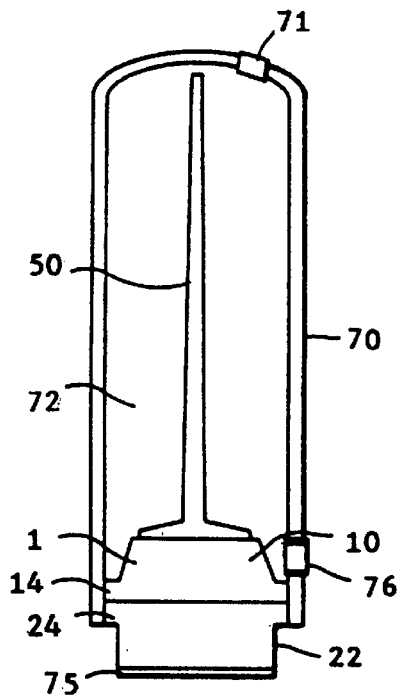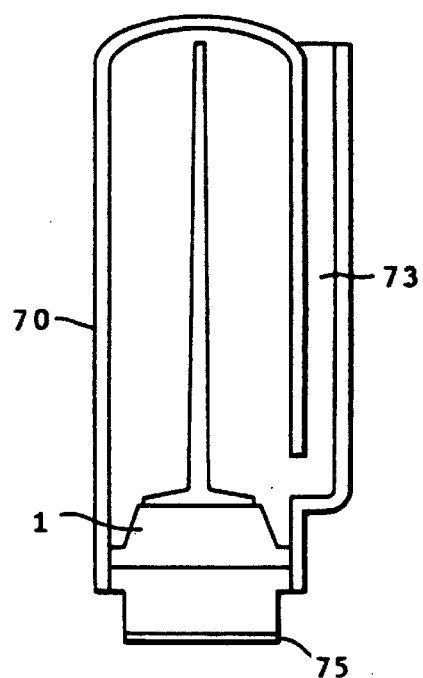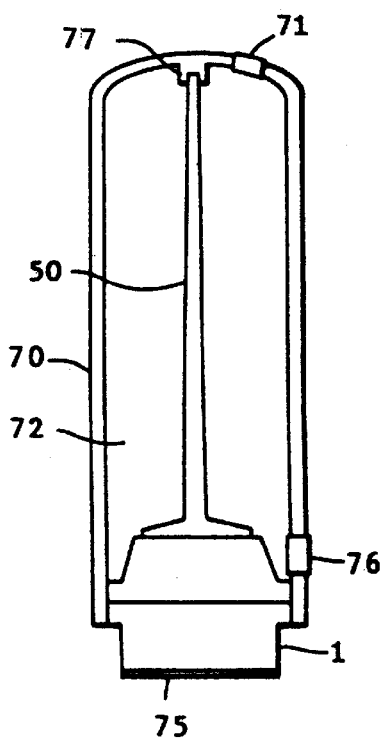

BLOOD FILTER UNIT

BACKGROUND OF THE INVENTION

This invention relates to a blood filter unit for the preparation of a plasma or serum sample from whole blood, and a plasma- or serum-collecting device using it.

The type or concentration of blood components, such as metabolites, proteins, lipids, electrolytes, enzymes, antigens, and antibodies, is measured, in general, using a plasma or serum sample obtained by centrifuging whole blood. However, centrifuging takes labor and time. Particularly, centrifuging is unsuitable for an urgent case of measuring a small number of samples promptly and in site inspection, because of requiring a centrifuge and electricity. Thereupon, it has been investigated to separate serum from whole blood by filtration.

Several filtration methods using glass fiber filter have been developed wherein whole blood is charged into the glass fiber put in a column from one side of the column, and pressurized or evacuated to obtain plasma or serum from the other side (Japanese Patent KOKOKU Nos. 44-14673, 5-52463, Japanese Patent KOKAI Nos. 2-208565, 4-208856).

However, practical filtration methods capable of obtaining an amount of plasma or serum from whole blood necessary for measuring by an automatic analyzer have not been developed except a part of items, such as blood sugar.

On the other hand, the inventors developed a blood filter unit composed of a filter holder and a syringe. The filter holder is composed of a holder body which contains filter material and a cap which is screwed on the holder body. The filter material consists of, e.g. two sheets of glass fiber filter, one sheet of cellulose filter and one sheet of polysulfone microporous membrane (FIG. 1 of EP 785430 A1)

Another blood filter unit composed of a holder body and a cap was also developed. The holder body consists of a plasma receiver located on the upper side and a filter chamber located on the underside. The filter material put in the filter chamber is composed of six sheets of glass fiber filter and one sheet of polysulfone microporous membrane (Example 1 of EP 785012A1).

These blood filter units have a problem in handling. That is, drawn blood is put in a blood collecting tube, and transported. Upon conducting blood analysis, a cap of the blood collecting tube is taken off, and a suction nozzle of the blood filter unit is inserted into the blood collecting tube. However, this manner adds load to workers in assay laboratories where a lot of blood samples are analyzed. Moreover, a suction apparatus is necessary for suction filtration of blood using the blood filter unit, and accordingly, the place conducting blood filtration is restricted.

It is also a problem that agglutinates of blood cells gradually deposited clog the suction nozzle during filtering blood.

SUMMARY OF THE INVENTION

An object of the invention is to provide a blood filter unit and a plasma- or serum-collecting device capable of obtaining a necessary volume of a plasma or serum sample from blood to be assayed easily at any place.

Another object of the invention is to provide a blood filter unit and a plasma- or serum-collecting device capable of continuing blood filtration without clogging the suction nozzle.

As a result of investigating eagerly, the inventors devised a blood filter unit comprising a blood filtering material and a holder accommodating the blood filtering material and having a nozzle for sucking blood and a filtrate outlet, and the inside of the holder being kept reduced pressure conditions which has achieved the above object.

The inventors also devised a blood filter unit comprising a blood filtering material and a holder accommodating the blood filtering material and having a nozzle for sucking blood and a filtrate outlet, and the inside of the holder being kept reduced pressure conditions, wherein the container has a space capable of containing the drawn blood without the end opening of the suction nozzle and the filtrate outlet in the blood, can be turned to dip the end of the suction nozzle in the drawn blood without spilling the blood.

The inventors further devised a blood filter unit comprising a blood filtering material and a holder accommodating the blood filtering material and having a nozzle for sucking blood and a filtrate outlet, and the inside of the holder being kept reduced pressure conditions, wherein the container is provided with an agglutinate checking member which restricts the movement of the agglutinate of blood cells.

BRIEF DESCRIPTION OF DRAWINGS

FIGS. 9–15 are sectional views each illustrating a state that the above blood filter unit is placed in a turnable container.

Figure 1:
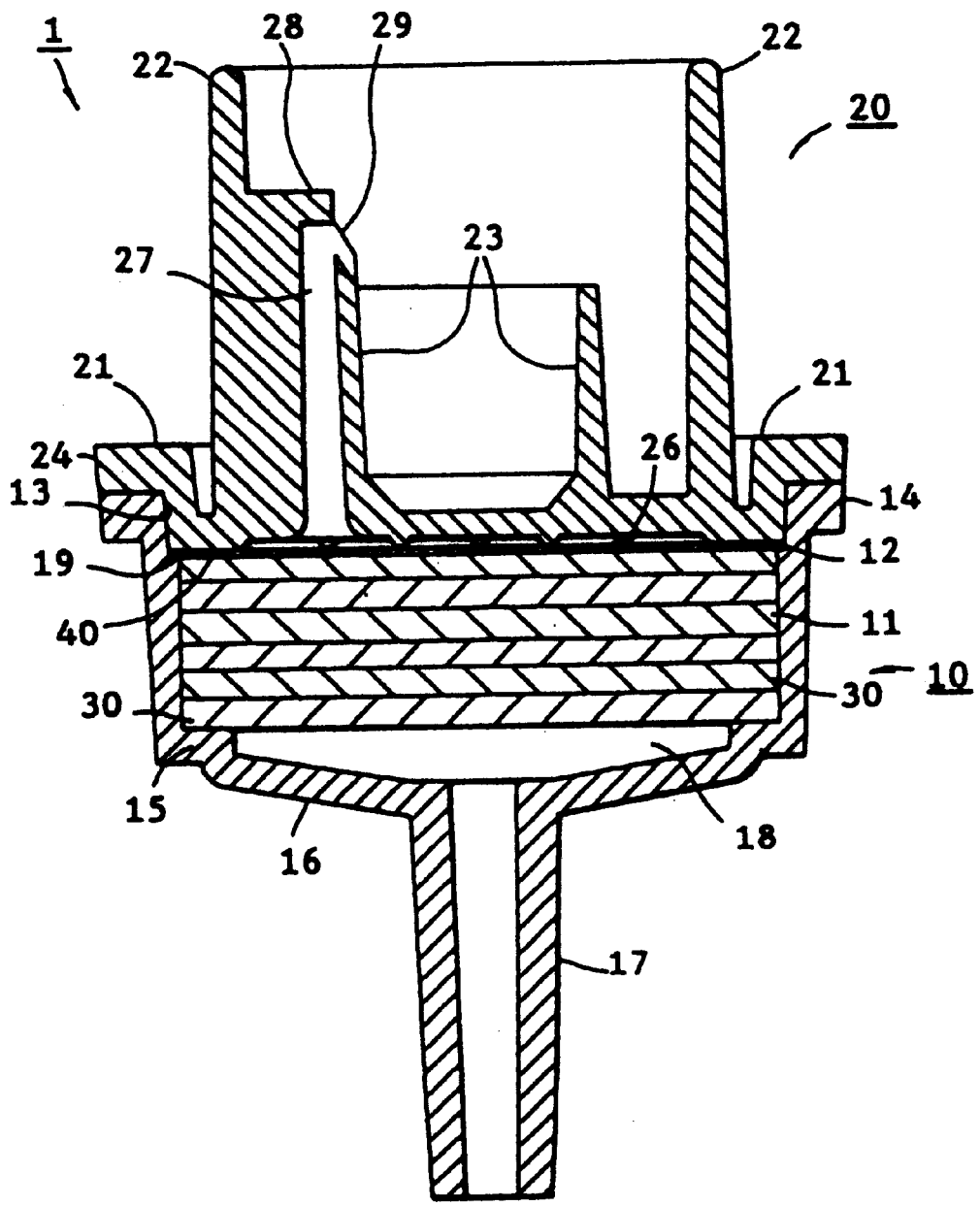
FIG. 1 is a longitudinal section of a blood filter unit used in the invention.

1 . . . Blood filter unit
10 . . . Holder body
11 . . . Glass fiber filter chamber
12 . . . Microporous membrane chamber
13 . . . Inclined portion
14 . . . Flange
15 . . . Glass fiber filter-placing portion
16 . . . Funnel-shaped disc portion
17 . . . Blood inlet
19 . . . Step portion
20 . . . Cap
21 . . . Outer wall
22 . . . Inner wall
23 . . . Cup
24 . . . Flange
25 . . . Rib
26 . . . Projection
27 . . . Filtrate passage
28 . . . Pent roof
29 . . . Discharge port
30 . . . Glass fiber filter
40 . . . Polysulfone microporous membrane
50 . . . Suction nozzle 51 . . . Large diameter portion
60 . . . Vacuum blood collecting tube (container)
61 . . . Plug (closing material)
62 . . . Sheet (closing material)
63 . . . Sheet (closing material)
64 . . . Pull tab
65 . . . Cap (closing material)
66 . . . Wax (closing material)
67 . . . Ferromagnetic material (closing material)
68 . . . Stopper
70 . . . Container (vacuum blood collecting tube, etc.)
71 . . . Rubber plug
72 . . . Space
73 . . . Passage
74 . . . Opening
75 . . . Sealing member
76 . . . Rubber plug
77 . . . Plug
80 . . . Agglutinate checking member
81 . . . Hanger

DETAILED DESCRIPTION OF THE INVENTION

Although the type of the blood filtering material is not limited, in the filtering material of tile invention, it is though that the filter material to be used does not trap blood cells only by the surface, but catches to remove blood cells gradually by entangiing at first large blood cell components and then smaller blood cell components in the space structure with permeating in the thickness direction in total of the filtering material, called the volumetric filtration. Preferable blood filtering material are glass fiber filter, microporous membrane, and the like, and a combination of glass fiber filter and microporous membrane is particularly preferred.

Preferable glass fiber filter has a density of about 0.02 to 0.5 g/cm$^3$, preferably about 0.03 to 0.2 g/cm$^3$, more preferably about 0.05 to 0.13 g/cm$^3$, a retainable particle size of about 0.6 to 9 μm preferably 1 to 5 μm. By treating the surface of glass fiber with hydrophilic polymer as disclosed in Japanese Patent KOKAI Nos. 2-208676, 4-208856, filtration proceeds more fast and smoothly. Lectin or other reactive reagent or modifier may be incorporated into glass fiber, or glass fiber may be treated therewith. Two or more glass fiber filters may be superimposed.

Microporous membranes having blood cel-separating ability of which the surface has been made hydrophilic separate whole blood into blood cells and plasma specifically without hemolysis to the degree of substantially influencing analytical values. A suitable pore size of the microporous membrane is smaller than the retaining particle size of glass fiber filter, and is 0.2 μm or more, preferably about 0.3 to 5 μm, more preferably about 0.5 to 4.5 μm, particularly preferably about 1 to 3 μm. The void content of the microporous membrane is preferably higher, and a suitable void content is about 40 to 95%, preferably about 50 to 95%, more preferably about 70 to 95%. Illustrative of the microporous membranes are polysulfone membrane, fluorine-containing polymer membrane, etc. The surface of the membrane may be hydrolyzed or may be rendered hydrophilic by a hydrophilic polymer or an activating agent.

Preferable microporous membranes are polysultone membrane, cellulose acetate membrane and the like, and particularly preferred one is polysulfone membrane.

As the fluorine-containing polymer membrane, there are the microporous matrix membrane (microporous layer) composed of polytetrafluoroethylene fibrils (fines) disclosed in WO 87/02267, Gore-Tex (W. L. Gore and Associates), Zitex (Norton), Poreflon (Sumitomo Denki), etc. Other fluorine-containing polymer sheets usable as the microporous layer include polytetrafluoroethylene microporous membranes disclosed in U.S. Pat. No. 3,368,872 (Examples 3 and 4), U.S. Pat. No. 3,260,413 (Examples 3 and 4), U.S. Pat. No. 4,201,548, etc., polyvinylidenefluoride microporous membranes disclosed in U.S. Pat. No. 3,649,505 and the like.

It is well known that fluorine-containing polymer microporous membranes as it is have a low surface tension. As a result, when the membrane is used as the blood cell filtering layer, aqueous liquid samples are repelled and do not diffuse nor permeate over the surface or into the inside. In the invention, the above repelling problem has been resolved by incorporating a sufficient amount of surfactant for rendering the outer surface and the inner space surface of the fluorine-containing polymer microporous membrane substantially hydrophilic thereinto.

As the surfactant for rendering the fluorine-containing polymer microporous membrane hydrophilic, the surfactant may be nonionic, anionic, cationic or ampholytic. However, nonionic surfactants are advantageous for the multilayer analytical elements for analyzing whole blood samples, because nonionic surfactants have a relatively low hemolytic activity among the above surfactants. Suitable nonionic surfactants include alkylphenoxypolyethoxyethanol, alkylpolyether alcohol, polyethyleneglycol monoester, polyethyleneglycol diester, higher alcohol-ethylene oxide adduct (condensate), polyol ester-ethylene oxide adduct (condensate), higher fatty acid alkanol amide, etc.

The fluorine-containing polymer microporous membrane may be rendered hydrophilic by providing one or more water-insolubilized water-soluble polymers in its porous spaces. The water-soluble polymers include oxygen-containing hydro carbons, such as polyacrylamide, polyvinylpyrrolidone, polyvinylamine and polyethylenamine, negative charge-containing ones such as polyvinyl alcohol, polyethylene glycol, methyl cellulose, ethyl cellulose, hydroxyethyl cellulose and hydroxypropyl cellulose, nitrogen-containing ones, such as polyacrylic acid, polymetacrylic acid and polystyrene sulfonic acid, and the like. The water-insolubilization may be conducted by heat treatment, acetal-inducing treatment, esterification, chemical reaction by potassium dichromate, crosslinking by ionizable radiation, or the like. Details are disclosed in Japanese Patent KOKOKU Nos. 56-2094 and 56-16187.

The polysulfone microporous membrane can be prepared by dissolving polysulfone into dioxane, tetrahydrofuran, dimethylformamide, dimethylacetamide, N-methyl-2-pyrrolidone or a mixed solvent thereof to obtaine a raw liquid for forming film, casting into film by flowing directly into a coagulating solution, washing, and then drying. Details are disclosed in Japanese Patent KOKAI No. 62-27006. In addition, polysulfone microporous membranes are also disclosed in Japanese Patent KOKAI Nos. 56-012640, 56-586941, 56-154051, etc., and they are applicable to the invention. The polysulfone microporous membrane can be. rendered hydrophilic, similar to the fluorine-containing polymer, by incorporating surfactant or providing water-insolubilized water-soluble polymer.

As the other nonfibrous microporous membranes, blushed polymer membranes composed of a cellulose ester, such as cellulose acetate, cellulose acetate/butyrate or cellulose nitrate, disclosed in U.S. Pat. No. 3,992,158 or U.S. Pat. No. 1,421,341 are preferable. Microporous membranes of polyamide, such as 6-nylon or 6,6-nylon, or polyethylene, polypropylene, or the like are also usable. Other nonfibrous microporous membranes usable include continuous microspace-containing porous membranes where polymer particulates, glass particulates, diatomaceous earth or the like are joined by a hydrophilic or non-water-adsorptive polymer, such as disclosed in U.S. Pat. No. 3,992,158, and U.S. Pat. No. 4,258,001.

Suitable effective pore size of the nonfibrous microporous membrane is 0.2 to 10 $\mu$m, preferably 0.3 to 5 $\mu$m, particularly preferably 0.5 to 5 $\mu$m. The effective pore size of the nonfibrous porous membrane in the invention is the pore size measured by the bubble point method according to ASTM F316-70. In the case that the nonfibrous porous membrane in a membrane filter composed of blushed polymer prepared by the phase separation method, the liquid passages in the thickness direction are, in general, the narrowest at the free surface (glossy face) in the manufacturing process of the membrane, and the, pore size in section of each liquid passage stipulated a circle is the smallest near the free surface. The minimum pore size of passages in the thickness direction per unit area has a distribution in facial direction of the membrane filter, and the maximum value determines filtration performance. In general, it is determined by the limit bubble point method.

As mentioned above, in the membrane filter composed of blushed polymer prepared by the phase separation method, liquid passages in the thickness direction become the narrowest at the free surface (glossy face) in the manufacturing process of the membrane. In the case of using the membrane as the nonfibrous porous membrane of the filtering material of the invention, it is preferable to face the glossy face of the membrane filter toward the side to discharge the plasma portion.

A third filtering material may be incorporated into the blood filtering material. The third filtering material may be filter paper, nonwoven fabric, woven fabric such as plain weave fabric, knitted fabric such as tricot fabric, etc. Among them, woven fabric and knitted fabric are preferred. The woven fabric or the like may be treated by glow discharge as disclosed in Japanese Patent KOKAI No. 57-66359. The third filtering material is preferably interposed between the glass fiber filter and the microporous membrane.

Preferable microporous membranes are polysultone membrane, cellulose acetate membrane and the like, and particularly preferred one is polysulfone membrane. In the blood filtering material of the invention, the glass fiber filter is located on the blood inlet side and the microporous membrane in located on the filtrate outlet side. The most preferable blood filtering material is a laminate of the glass fiber filter and polysulfone membrane laminated in this order from the blood inlet side.

Respective layers may be integrated by joining each other using partially disposed (e.g. spots) adhesive, according to disclosures in Japanese Patent KOKAI Nos. 62-138756-8, 2-105043, 3-16651, etc.

The quantity of whole blood filterable by this system is greatly influenced by the void volume existing in glass fiber filter and the volume of blood cells in the whole blood. When the density of the glass fiber filter is high (pure size to retain particles is small), erythrocytes are trapped in the vicinity of glass fiber filter surface, voids in the glass fiber filter are clogged in a very thin region from the surface, and accordingly, filtration does not proceed thereafter. As a result, recovered plasma volume by filtration is small. On that occasion, when the filter material is sucked by stronger suction in order to increase recovered plasma volume, blood cells are destroyed, i.e. hemolyzed. That is, the filtration becomes similar to surface filtration, and utilization rate of void volume of the filter is low.

As an indicator corresponding to void volume or filtrate volume of plasma, water permeation speed is suitable. The water permeation speed is determined by putting a glass fiber filter with a definite area in a closed filter unit of which the inlet and outlet can be connected by a tube, adding a definite volume of water, and pressurizing or sucking at a constant pressure. The water permeation speed is filtrate volume per unite area and time, and expressed by ml/sec.

For example, glass fiber filter 20 mm $\phi$ in diameter is put in a filter unit, and a 100 ml syringe containing 60 ml water is connected to the top of the filter unit. Water flows down naturally, and volume of water passing through the glass filter from 10 sec to 40 sec after starting is measured as the water permeation volume, and the water permeation speed per unit area is calculated from it.

Glass fiber filters particularly suitable for plasma separation are having a water permeation speed of about 1.0 to 1.3 ml/sec, and illustrative of the glass fiber filters are Whatman GF/D, Toyo Roshi GA-100, GA-200 and the like. Furthermore, the glass fiber filter can be prepared by suspending glass fibers of a commercial glass fiber filter in hot water, and then making the glass fibers into a low density sheet (density: about 0.03 g/cm$^3$) on a nylon net. The glass fiber filter thus prepared shows good plasma separating ability.

A suitable thickness of the glass fiber filter varies according to the plasma volume to be recovered and density (void content) and area of the glass fiber filter. A necessary amount of plasma for analyzing plural items using dry analytical elements is 100 to 500 $\mu$l. In practical viewpoint, a glass fiber filter having a density of about 0.02 to 0.2 g/cm$^3$ and an area of 1 to 5 cm$^2$ is suitable. In this case, a suitable thickness of the glass fiber filter is about 1 to 10 mm, preferably about 2 to 8 mm, more preferably about 4 to 6 mm. The above thickness can be made by superposing 1 to 10 sheets, preferably 2 to 8 sheets of glass fiber filter.

A suitable thickness of the microporous membrane is about 0.05 to 0.5 mm, preferably about 0.1 to 0.3 mm, and the number of the microporous membrane is usually one. However, two or more sheets of microporous membrane may be used, if necessary.

In the case of blood filter unit, the blood filtering material is placed in a holder having a blood inlet and a plasma outlet. The holder is, in general, formed of a body accommodating the blood filtering material and a cap, and each of them is provided with at least one aperture. One is used as the blood inlet, and the other is used as the plasma outlet, optionally further as a suction port. A suction port may be provided separately. In the case that the holder is rectangular and is provided with the cap on a side of the holder, both of the blood inlet and the plasma outlet may be provided on the holder body.

The volume of the filter chamber which accommodates the blood filtering material is necessary to be greater than the total volume of the blood filtering material both in a dry state and in a swelled state upon absorbing a sample (whole blood). When the volume of the filter chamber is smaller than the total volume of the blood filtering material, filtration does not proceed efficiently and hemolysis occurs. A suitable ratio of the volume of the filter chamber to the total volume of the blood filtering material in a dry state is, in general, 101 to 200%, preferably 110 to 150%, more preferably 120 to 140%, although the ratio varies according to the swelling degree of the filtering material. An actual volume is set depending on the necessary amount of plasma or serum, and is about 0.5 to 2.5 ml, usually about 0.6 to 2 ml, especially about 0.7 to 1.5 ml.

Besides, it is preferable that the periphery of the blood filtering material is closely fitted to the wall of the filter chamber so as not to form a bypass of whole blood without passing the filtering material.

The suction nozzle for sucking blood is connected to the blood inlet of the holder. The nozzle may be integral with or separate from the holder. In the case of a separate body, the nozzle is fixed to the holder body, and the connecting portion has a closed structure. The connecting means may be adhesion, fusion, screwing, fitting or the like.

The blood filter unit is made into a closed structure except the blood inlet and the plasma outlet by attaching a cap to the holder body.

As the material of the holder, thermoplastic or thermosetting plastics are preferable. Illustrative of the plastics are general-purpose plystyrene, high impact polystyrene, methacrylate resin, polyethylene, polypropylene, polyester, nylon, polycarbonate, etc. The material may be transparent or opaque.

Fitting of the cap to the holder body may be any means, such as adhesion using adhesive or fusion welding. On that occasion, either periphery of the holder body or of the cap is located on the inside, or both peripheries are butted. The fitting may be in a state of detachable utilizing screws or the like.

The shape of the blood filtering material is not restricted, but disc and polygon is preferable in view of production. By rendering the size of the blood filtering material slightly greater than the inside section of the holder body (i.e. filter chamber), breakthrough of blood at the periphery of the filtering material can be prevented. To render the shape square is preferable because of no generation of cutting loss. Moreover, cut pieces of glass fiber filter can also be served.

In the blood filter unit of the invention, the opening of the nozzle for sucking blood and the filtrate outlet are sealed in an openable state, and the inside of the holder is kept reduced pressure conditions. Hereupon, "sealed" means that the inside of the holder is made airtight state, and opening in "openable state" means to release the airtight state to connect to external air.

In an aspect, the sealing is carried out by closing the opening of the nozzle and the filtrate outlet in an easily openable state.

The closing of the filtrate outlet is conducted by attaching a cap or plug to the outlet, sticking a sheet or film onto the outlet, or the like. Attaching of the cap is screwing, fitting, adhering, welding or the like, and sticking of the sheet or film is adhering, welding or the like. Suitable closing materials, such as, cap, plug, sheet and film, can intercept air for a long period, and illustrative of the materials for the cap are polyvinylidene chloride, polypropylene, high density polyethylene, polyethylene terephthalate, nylon, composite laminated films of a thermoplastic film and an aluminum foil and the like. Illustrative of the materials for the plug are various rubbers, and illustrative of the material for the sheet or film are polyvinylidene chloride, polypropylene, high density polyethylene and laminates containing a metal foil or deposited membrane, such as aluminum, are especially preferred. In the case of the sheet or film, a suitable thickness is about 0.01 to 0.2 mm, preferably about 0.07 to 0.15 mm. When the whole body of the blood filter unit is placed in a container of which the inside is kept reduced pressure conditions, the airtightness required of the closing material is not so strictly, and it is enough to keep reduced pressure conditions for about 10 minutes after breaking the reduced pressure conditions of the container. It is preferable that the closing material is ruptured by sticking a needle or slender bar, preferably descending of a sampling nozzle of an analyzer, upon analyzing the plasma or serum obtained by the filtration.

When a suction port is provided separate from the filtrate outlet, it is necessary to close both of the suction port and the filtrate outlet.

The closing of the nozzle for sucking blood is necessary to be released after entering the end opening of the suction nozzle in blood. For example, in the case that a cap or plug is attached to the end opening of the nozzle, the cap or plug can be detached by pulling a string or the like which has previously been fixed to the cap or plug after entering the end opening in blood. Another means is to fix the cap or plug to the container for containing blood, and the cap or plug is detached by moving the container or the cap or plug in the detaching direction of the cap or plug. Another means is to adhere a film or sheet to the end opening and the film or sheet is broken by sticking a projection provided on the bottom of the container. The above closing materials can be chosen from those of the filtrate outlet mentioned previously. Still another means is to make the cap or plug of a ferromagnetic material or a thermosoftening material such as wax, and the cap or plug is detached by a magnet a heating.

The area to be made reduced pressure is at least capable of sucking blood, passing it through blood filtering material and entering the filtrate into a filtrate reservoir, i.e. a space from the suction nozzle to the filtrate reservoir through a blood filtering material chamber. The degree of reduced pressure is at least capable of filtering a necessary volume of blood, and in practical viewpoint, a suitable pressure is about −300 to −700 mm Hg, preferably about −500 to −650 mm Hg. However, the suitable pressure varies according to the structure of the blood filter unit, and it is preferably set through a preliminary test.

It is preferable that the blood filter unit is previously placed in a container for containing drawn blood. As the container, for example, a commercial blood collecting tube can be used. The inside of the container is shielded from external air by attaching a cap, a plug or the like or sticking a sheet, a film or the like, or so on. The inside of the container can be made reduced pressure conditions by making a closed structure with the cap, plug, sheet, film or the like. On that occasion, it is possible that the opening of the nozzle for sucking blood is opened and drawn blood is injected into the container by sticking the needle of the syringe into the container through the sheet, film, plug or the like.

In another aspect of the invention, the container is made turnable. In this case, the container has a space capable of containing the drawn blood without dipping the end opening of the suction nozzle and the filtrate outlet in the blood, and can be turned to dip the end of the suction nozzle in the drawn blood without spilling the blood from the container.

Some embodiments of such a container are illustrated in FIGS. 9–14.

The container 70 of FIG. 9 is in a form of an inverted test tube provided with a circle hole on the top which is closed by fitting a rubber plug 71. The blood filter unit 1 is fitted to the bottom opening of the container 70. The end of the inner wall 22 of the blood filter unit 1 is sealed by adhering a sealing member 75, and the periphery of the flanges 14, 24 are closely fitted to the inner wall of the container 70 to form a sealed state. When serving the container 70, the needle of a blood collecting device (not illustrated) is sticked through the rubber plug 71. Then, the drawn blood is sucked to enter the container 70 by the reduced pressure in the container 70. The container 70 is turned upside down, and the rubber plug 76 fitted to the side wall of the container near the bottom is taken off. Since the end opening of the suction nozzle 50 is located near the top which has become the bottom by the turning, the blood in the container 70 is pushed by the air entered from the outside to enter the blood filter unit 1 of which the inside is in reduced pressure conditions, and blood filtration is carried out to obtain plasma or serum. The pore formed by sticking the needle of the syringe is closed by the elasticity of the rubber plug 71, and therefore, the blood does not leak out. The rubber plug may be that of 76 alone, and blood is injected therethough. The plasma or serum thus obtained can be subjected to analysis by removing the sealing member 75 or sticking a needle to suck it.

The turnable container requires that the bottom is closed, and the bottom may be closed by attaching a seal plate. On that occasion, the suction nozzle 50 enters the space 72 for containing blood perpetrated through the real plate. The rubber plug 71 may be located on the side wall instead of the top or both of the side wall and the top.

The container 70 of FIG. 10 is provided with a passage 73 having a connecting port to the inside of the container near the bottom instead of the rubber plug 71 as the blood inlet of the container 70. The connecting port is formed at a height where blood does not escape through the passage 73 upon turning the container 70 upside down.

The container 70 of FIG. 11 is provided with a plug 77 for closing the end opening of the suction nozzle 50 at the inside top of the container 70 of FIG. 9. The blood filter unit 1 is sealed by the sealing material 75 adhered to the end of the inner wall 22 and the plug 77, and the inside of the blood filter unit 1 is made higher reduced pressure than the space 72 of the container 70. Blood filtration can be carried out by turning the container 70, taking off the rubber plug 77, and detaching the end opening of the suction nozzle 50 from the plug 77 by pulling upward the blood filter unit 1 slightly.

Figure 12:
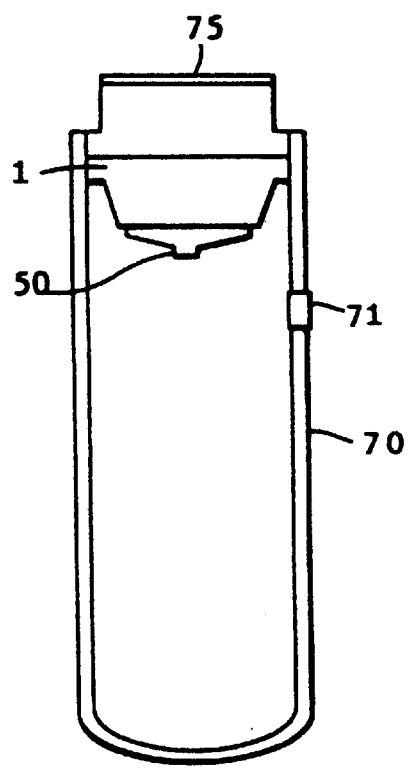

The container of FIG. 12 is a test tube in the normal state of the test tube of FIG. 9. The suction nozzle 50 is made very short, and the rubber plug 71 is attached to upper part of the side wall. The blood is drawn into the container 70 by sticking the needle of a blood collecting device through the rubber plug 71, and the blood is filtered by turning the container 70, while external air is introduced through the plug 71 portion by detaching it, sticking a needle or the like. In order to reduce dead space, a seal plate or the like which inhibits blood from entering the lower part than the end opening of the suction nozzle 50. The position of the rubber plug 71 may be moved.

Figure 13:
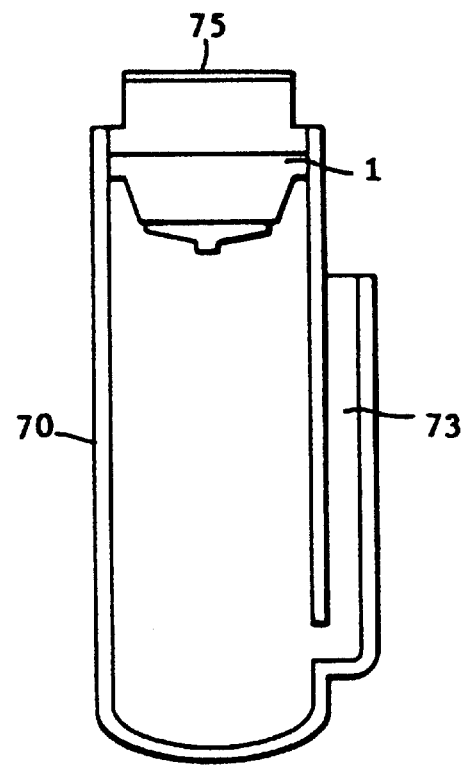

The container 70 of FIG. 13 is provided with a passage 73 instead of the rubber plug 71 similar to the container 70 of FIG. 10.

Figure 14:
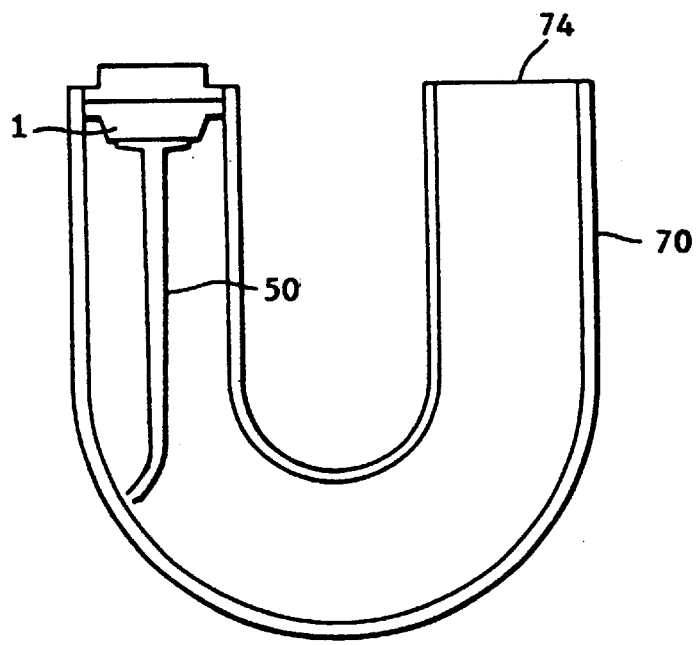
Figure 15:
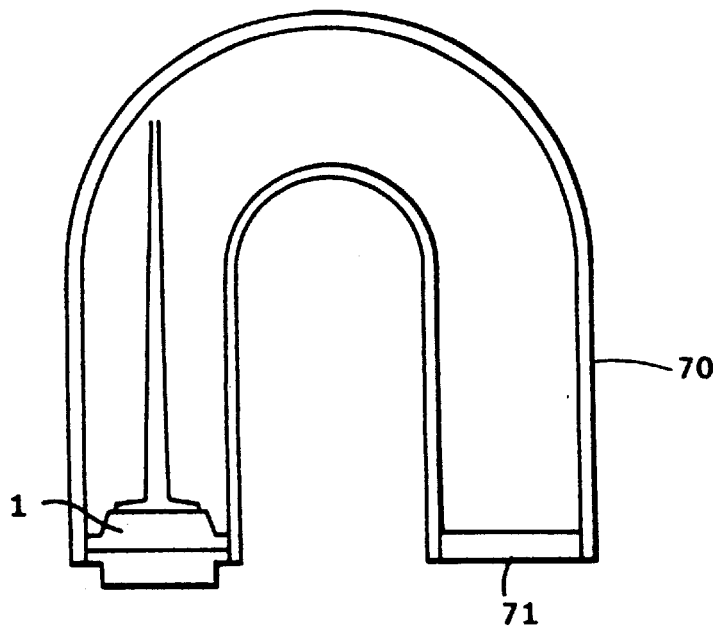

The container 70 of FIG. 14 is in a form of a U-shaped tube, and the blood filter unit 1 is fitted to one end opening of the U-shaped tube. Blood is put in the container 70 from the other end opening of the U-shaped, and blood filtration is carried out with inclining the U-shaped tube so that the end opening of the suction nozzle 50 becomes the lowermost.

The container 70 is an inverted U-shaped tube. The blood filter unit 1 is fitted to seal one end opening of the U-shaped tube, and a rubber plug 71 is fitted the seal the other end opening. Blood is drawn in the container 70 by sticking the needle of a blood collecting device through the rubber plug 71, and the blood is filtered in a turned state.

In another aspect of the invention, an agglutinate checking member is provided in the container. The agglutinate checking member restricts the movement of agglutinates by engaging them with projection(s), guiding the moving direction, increasing the resistance to passing agglutinates. The direction of the projection(s) is in the direction inhibiting the movement of agglutinates toward the end opening of the suction nozzle of the blood filter unit, and accordingly, the projection angle can be in a wide range. In general, the angle is about 60 to 150 degrees, preferably about 80 to 120 degrees upward from the depth direction of the container. The form of the projection is capable of inhibiting the movement of agglutinates, and many forms are possible, such as round rod, square rod, string, fiber, plate, screw, cone, square cone, polygonal line and the like. Each projection is projected radially in a form of brush, projected crossly in a form of lattice or net (the crossed portions may be joined or separated), projected randomly, to form a plate having a plurality of penetrated holes, such as perforated plate (sieve tray), punched plate, grating, or the like. A suitable distance between projections or a suitable diameter of holes is about 0.2 to 2 mm, preferably about 0.4 to 1 mm. A suitable thickness of the projection can be in a wide range, such as about 0.1 to 5 mm, preferably about 0.1 to 3 mm. The number of the projections can also be in a wide range, and the greater number in a range capable of containing the blood filter unit is more preferable. In the case of perforated plate or net or lattice or the like, a suitable number of stairs about 1 to 10, preferably about 3 to 7. As to the arrangement of the projections, it is suitable to arrange the projections up to near the upper end of a scheduled amount of blood drawn.

It is preferable to accelerate the formation or growth of agglutinates by providing corners on the projections, placing a blood coagulant, such as thrombin, silica powder, glass powder or polyvinyl alcohol, in the container. The blood coagulant is preferably applied to the inner wall surface, the surface of the projections or the like, although it is effective by mere placing it in the container, a suitable coating amount is about 1000 to 4000 KIU per one container for thrombin, and about 0.01 to 2 wt % for silica powder.

EXAMPLES

Example 1

Figure 2:
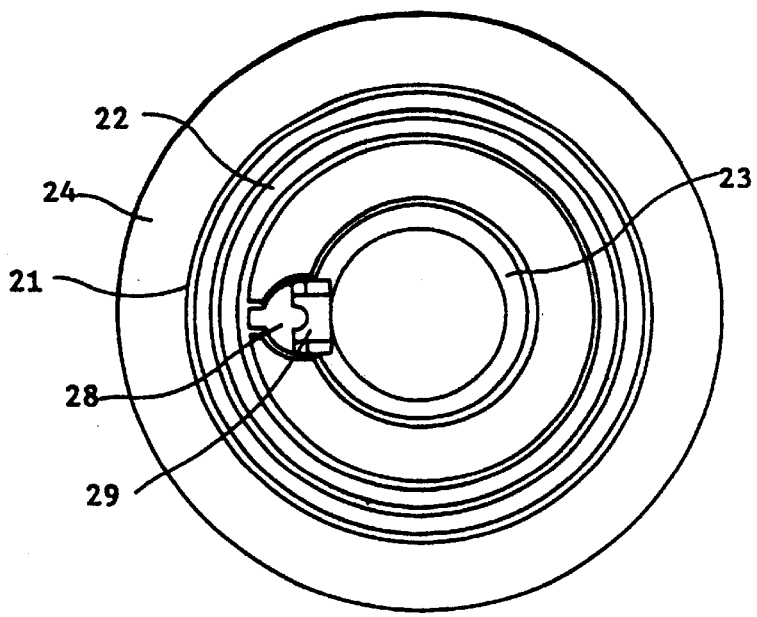
FIG. 2 is a plan view of the cap of the unit.
Figure 3:
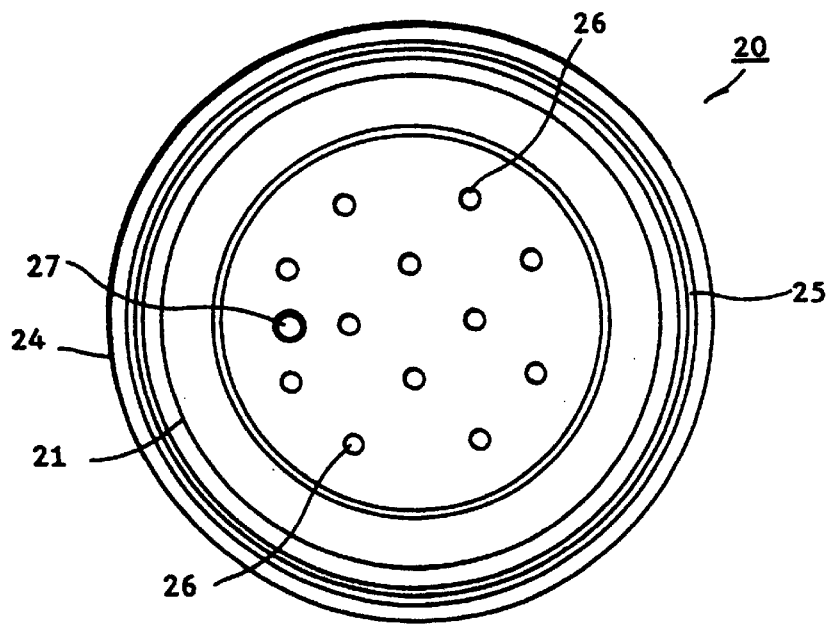
FIG. 3 is a bottom view thereof.

A blood filter unit illustrated in FIGS. 1–3 was prepared. FIG. 1 is a longitudinal section of the blood filter unit in the assembled state, FIG. 2 is a plan view of the cap which constitutes the blood filter unit, and FIG. 3 is a bottom view thereof.

The blood filter unit is, as shown in FIG. 1, composed of a holder 1 consisting of a holder body 10 and a cap 20 and blood filtering material consisting of a glass fiber filter 30 and a microporous membrane 40.

The holder body 10 is made of high-impact polystyrene resin, and has a glass fiber filter chamber 11 for containing the glass fiber filter 30 and a microporous membrane chamber 12 for containing a polysulfone microporous membrane as the microporous membrane 40 above the glass fiber filter chamber 11. The microporous membrane has a diameter greater than the glass fiber filter chamber, and the periphery of the microporous membrane 40 is nipped by the step portion 19 formed on the foundary between the glass fiber filter chamber 11 and the microporous membrane chamber 12 and the bottom of the cap 20 so as not to form a leakage without passing the blood filtering material. An inclined portion 13 which stands upward slightly obliquely is formed at the outer periphery of the step portion 19, and a flange 14 is formed outward at the upper end of the inclined portion 13.

On the other hand, the bottom of the holder body 10 is in the form of a shallow funnel, and a step portion is formed as a glass fiber filter-placing portion 15 at the periphery of the funnel-shaped disc portion 16. A nozzle-shaped blood inlet 17 is formed downward as the supply port of liquid to be filtered at the center of the funnel-shaped disc portion 16. A suction nozzle (not illustrated) is fitted to the nozzle-shaped blood inlet 17. The glass fiber filter-placing portion 15 also functions as a spacer which separates the glass fiber, filter 30 from the bottom and forms a space 18 for spreading the liquid to be filtered over the whole surface of the glass fiber filter 30.

The cap 20 has an outer wall 21 and an inner wall 22 formed concentrically and a cup 23 as the receiver of the filtrate. The outer wall 21 is in the form of a taper having the same inclination angle as the inclined portion 13, and the outside diameter of the outer wall 21 is the same as the inside diameter of the inclined portion 13. That is, the outer wall 21 is fitable to the inclined 13 in a sealed state. A flange 24 is formed outward at the periphery of the outer wall 21, and the flange 24 is bonded to the flange 14 of the holder body, 10 by ultrasonic welding. As shown in FIG. 3, a rib 25 is formed on the underside of the flange 24 so as to concentrate the ultrasonic energy there to be bonded to each other to ensure sealing. The rib 25 disappears after bonding.

As shown in FIG. 3, twelve projections 26 are formed at the bottom of the cap 20 at almost regular intervals. The projection 26 prevent the polysulfone microporous membrane 40 from adhering to the bottom.

A chimney-shaped filtrate passage 27 is formed upward penetrating the bottom of the cap 20, and a pent roof 28 is formed horizontally at the upper end of the filtrate passage 27 so as to prevent spouting of the filtrate, The pent roof 28 has the form of a combination of two half circles, as shown in FIG. 2, and the periphery of the large half circle conforms to the periphery of the filtrate passage 27. The periphery of the filtrate passage 27. The discharge port 29 of the filtrate is provide obliquely at the upper end of the filtrate passage 27, and has the form of a lower half ellipse.

The above blood filter unit has a diameter of the glass fiber filter chamber 11 of 20.1 mm and a depth thereof of 5.9 mm, a diameter of the microporous membrane chamber 12 of 21.0 mm, a diameter of the upper end of the inclined portion of 22.5 mm and a depth thereof of 2.10 mm, a diameter at the lower end of the outer periphery of the outer wall 21 of 20.98 mm and a height between the underside thereof and the flange 24 of 2.0 mm, an inside diameter of the inner wall 22 of 15.0 mm, and an inside diameter of the cup 23 of 7.5 mm. The glass fiber filter 30 consists of six glass fiber filter sheets each having a diameter of 20.0 mm and a thickness of 0.91 mm, and the microporous membrane consists of one polysulfone microporous membrane having a diameter of 20.9 mm and a thickness of 150 μm.

Figure 4:
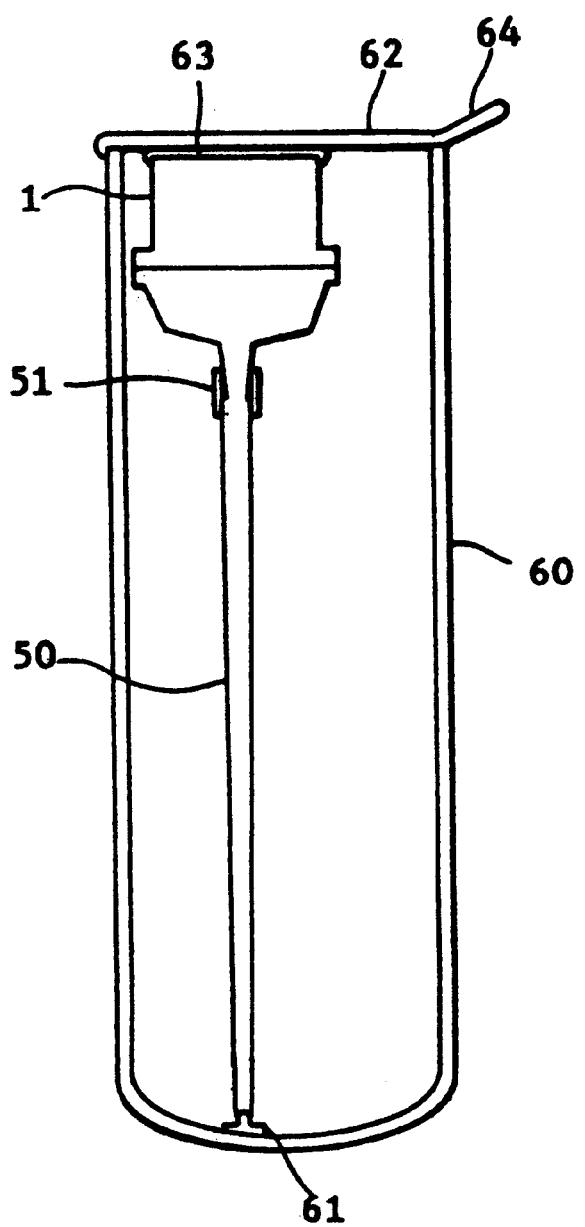
FIG. 4 is a longitudinal section illustrating a state that the above blood filter unit is placed in a vacuum blood collecting tube.
Figure 5:
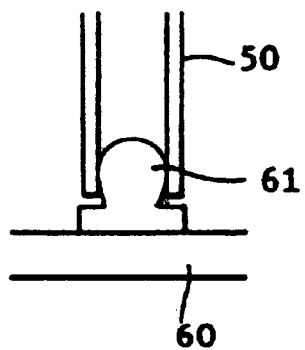
FIGS. 5–8 are sectional views each illustrating a closing material for closing the end opening of a suction nozzle.
Figure 6:
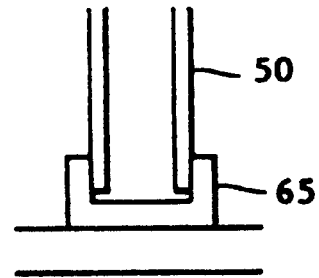

A suction nozzle 50 as shown in FIGS. 4–5 is fitted to the nozzle-shaped blood inlet 17. The suction nozzle 50 is in the form of a slender truncated cone-shaped cylinder, and the upper end of the suction nozzle 50 is enlarged with a step to form a large diameter portion 51. The suction nozzle 50 is made of polypropylene resin.

The blood filter unit 1 is, as shown in FIG. 4, put in a vacuum blood collecting tube 60. The vacuum blood collecting tube 60 is made of polyethylene terephthalate, and a plug 61 made of polyethylene terephthalate which is fitted to close the end opening of the suction nozzle 50 is bonded to the bottom of the blood collecting tube 60.

The end opening of the suction nozzle 50 was fitted to the plug 61, and the inside of the blood filter unit 1 was evacuated, and a sheet 63 was adhered to close the end opening of the inner wall 22. Then, the inside of the blood collecting tube 60 was evacuated, and a sheet 62 was adhered to close the opening of the blood collecting tube 60. Both of the sheets 62, 63 were a composite film consisting of an aluminum foil and a polyester film 0.12 mm in thickness. The adhesion was carried out by hot pressing. The inside pressure of the vacuum blood collecting tube 60 was −700 mm Hg, and that of the blood filter unit 1 was −650 mm Hg. The sheet 62 for closing the blood collecting tube 60 was provided with a pull tab 64 used for peeling it.

Figure 7:
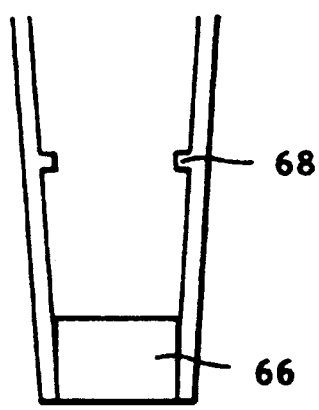
Figure 8:
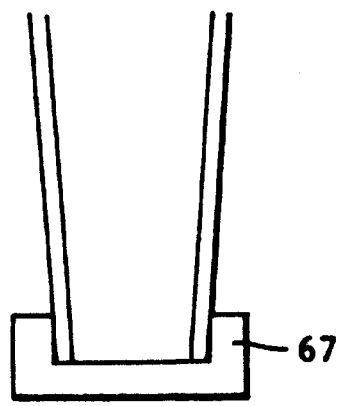

The end opening of the suction nozzle 50 can be closed by a cap 65 bonded to the bottom of the blood collecting tube 60. The end opening can also be closed by wax 66 as shown in FIG. 7, or a ferromagnetic material as shown in FIG. 8. 68 in FIG. 7 is a stopper of the wax 66.

By bonding the sheet 63 to the sheet 62 in the embodiment of FIG. 4, the end opening of the suction nozzle 50 can be detached from the plug 61 by the peeling motion of the sheet 62.

Example 2

The same blood filter 1 as employed in Example 1 was used.

The end opening of the inner wall 22 was closed by attaching a rubber sheet as the sealing member 75, and the blood filter unit 1 was fitted into the opening of the vacuum blood collecting tube 70 shown in FIG. 9 in a vacuum chamber. The fitting portion was sealed by applying a sealant. The needle of a blood collector was stuck into the rubber plug 71 located on the top of the blood collecting tube 70, and blood was drawn into the tube 70 and the needle was pulled off. After leaving the tube 70 for about 30 minutes, the tube 70 was turned, and the rubber plug 76 located on the side wall was detached. Thus, the blood in the tube was filtered by the blood filter unit 1. If a part of the blood remained, the rubber seal 75 was removed, and a suction apparatus having a vacuum pump was connected to the inner wall 22. Then, the suction pump was worked to conduct blood filtration, and serum was accumulated in the cup 23 of the blood filter unit 1.

Example 3

The same blood filter 1 as employed in Example 1 was used. The suction nozzle 50 was made of polyethylene.

Figure 16:
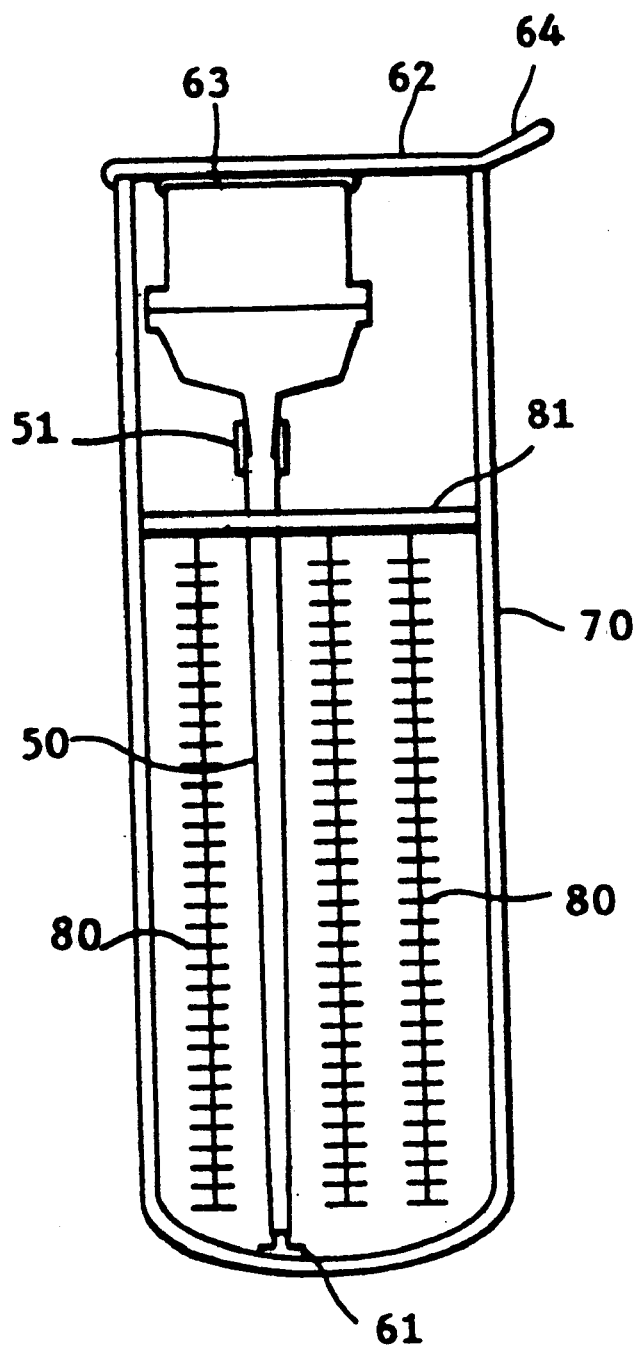
FIGS. 16–18 are sectional views each illustration a state that the above blood filter unit is placed in a vacuum blood collecting tube provided with an agglutinate checking member.

The blood filter unit 1 was put in a vacuum blood collecting tube 70, as shown in FIG. 16. The blood collecting tube was made of polyester having a diameter of 30 mm, and a plug 61 made of polycarbonate was bonded to the bottom for closing the end opening of the suction nozzle 50.

In the blood collecting tube 70, 20 strings of a brush-shaped agglutinate checking member 80 made of polypropylene were hanged down from a disc-shaped hanger 81. Each string of the agglutinate checking member 80 was formed of polypropylene wires 0.5 mm in diameter 70 mm in length planted radially, and the total length of the planted portion was 75 mm. The hanger 81 had a hole for penetrating the suction nozzle 50 of the blood filter unit 1 and a hole for penetrating the needle of a blood collector.

The end opening of the suction nozzle 50 was passed through the hole of the hanger 81, and fitted into the plug 61. Then, the inside of the blood filter unit 1 was evacuated, and a sheet 63 was adhered to close the end opening of the inner wall 22. Then, the inside of the blood collecting tube 70 was evacuated, and a sheet 62 was adhered to close the opening of the blood collecting tube 70. Both of the sheets 62, 63 were a composite film of polyester/aluminum/polyester 0.15 mm in thickness. The adhesion was carried out by heat sealing. The inside pressure of the blood filter unit 1 was −650 mm, and that of the blood collecting tube 1 was −300 mm Hg. The sheet for closing the blood collecting tube was provided with a pull tab 64 used for peeling it.

The needle of a blood collector was stuck into the blood collecting tube 70, and blood was drawn into the tube 70. The tube 70 was left for about 30 minutes. When a blood coagulant was put in the tube 70, the leaving period could be shortened. Agglutinates formed during the leaving were caught by the agglutinate checking member 80, and did not reach the end opening of the suction nozzle 50. When becoming this state, the end opening of the suction nozzle 50 was detached from the plug 61. The blood was filtered by the blood filter unit 1, and serum was accumulated in the cup 23 of the blood filter unit 1. When a prescribed volume of serum was collected, the upper sheet 63 was removed or punctured, and the serum was sucked by inserting a pipette.

Figure 17:
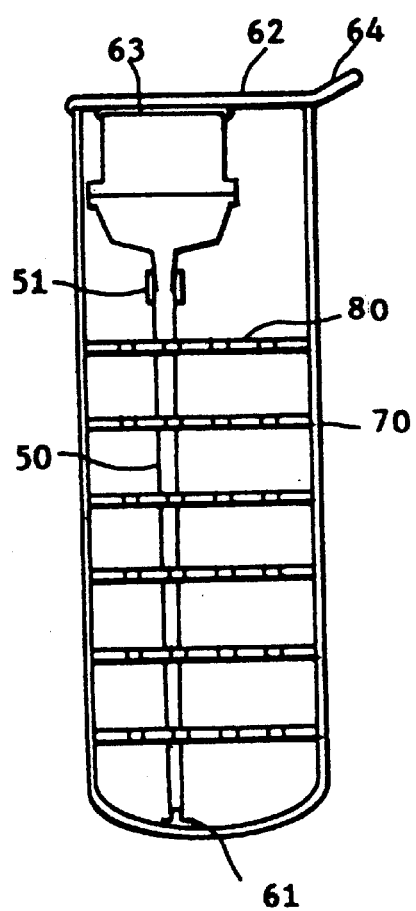
Figure 18:
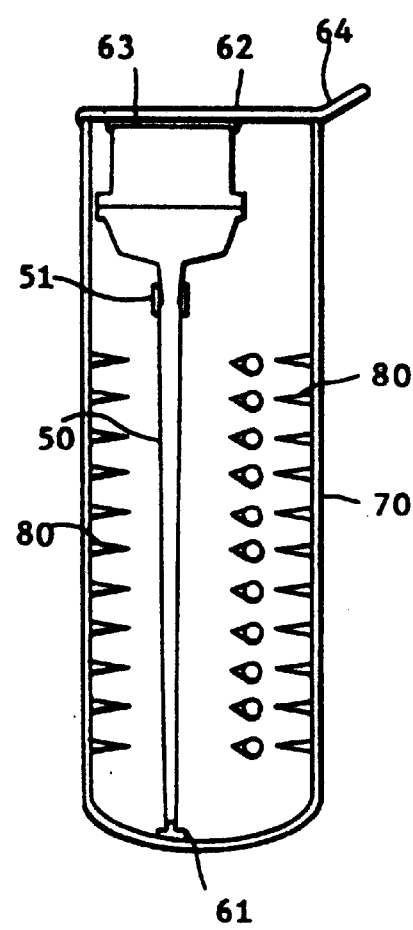

Other embodiments of the agglutinate checking member were illustrated in FIGS. 17 and 18. The agglutinate checking member of FIG. 17 was composed of sieve trays in six stairs. The agglutinate checking member of FIG. 18 was composed of a plurality of cone-shaped projections projected toward inside.

What is claimed:

1. A blood filter unit comprising:
   a blood filtering material and
   a holder accommodating the blood filtering material and having a nozzle for sucking blood and a filtrate outlet; wherein the blood filter unit is placed in a container for containing drawn blood, an inside of the container is kept under reduced pressure conditions, reduced pressure conditions are caused on an inside of the holder by the reduced pressure conditions of the container and the nozzle and the filtrate outlet are closed in an easily openable state.

2. A blood filter unit comprising:
   a blood filtering material and
   a holder accommodating the blood filtering material and having a nozzle for sucking blood and a filtrate outlet, wherein the blood filter unit is placed in a container for containing drawn blood, an inside of the container is kept under reduced pressure conditions, and reduced pressure conditions are caused on an inside of the holder by the reduced pressure conditions of the container, wherein the blood filtering material comprises a glass fiber filter and the holder is fixed to the container with a space capable of passing the drawn blood on the outside of the holder.

3. A blood filter unit comprising:
   a blood filtering material and
   a holder accommodating the blood filtering material and having a nozzle for sucking blood, a filtrate outlet and an inside being kept under reduced pressure conditions, wherein the blood filter unit is placed in a container for containing drawn blood, the container has a space capable of containing the drawn blood without dipping an end opening of the suction nozzle or an end opening of the filtrate outlet in the blood, and can be turned to dip the end opening of the suction nozzle in the drawn blood without spilling the blood, and wherein the blood filtering material comprises a glass fiber filter and the holder is fixed to the container.

4. A blood filter unit comprising:
   a blood filtering material and
   a holder accommodating the blood filtering material and having a nozzle for sucking blood, a filtrate outlet and an inside being kept under reduced pressure conditions; wherein the blood filter unit is placed in a container for containing drawn blood, the container has a space capable of containing the drawn blood without dipping an end opening of the suction nozzle or an end opening of the filtrate outlet in the blood, and can be turned to dip the end opening of the suction nozzle in the drawn blood without spilling the blood, and the nozzle and the filtrate outlet are closed in an easily openable state.

5. The blood filter unit of claim 3 wherein the inside pressure of the blood filter unit is −300 to −700 mm Hg as gauge pressure of vacuum.

6. A blood filter unit comprising:
   a blood filtering material and
   a holder accommodating the blood filtering material and having a nozzle for sucking blood, a filtrate outlet and an inside being kept under reduced pressure conditions, wherein the blood filter unit is placed in a container for containing drawn blood and the container is provided with an agglutinate checking member for restricting movement of an agglutinate of blood cells, and wherein the blood filtering material comprises a glass fiber filter and the holder is fixed to the container with a space capable of passing the drawn blood on the outside of the holder, and wherein the agglutinate checking member is located in the container but outside of the holder.

7. A blood filter unit comprising:
   a blood filtering material and
   a holder accommodating the blood filtering material and having a nozzle for sucking blood, a filtrate outlet and an inside being kept under reduced pressure conditions; wherein the blood filter unit is placed in a container for containing drawn blood, the container is provided with an agglutinate checking member for restricting movement of an agglutinate of blood cells and the nozzle and the filtrate outlet are closed in an easily openable state.

8. The blood filter unit of claim 6 wherein the inside pressure of the blood filter unit is −300 to −700 mm Hg as gauge pressure of vacuum.

9. The blood filtering unit of claim 2 wherein the blood filtering material consists essentially of a glass fiber filter and a microporous membrane.

10. The blood filtering unit of claim 3 wherein the blood filtering material consists essentially of a glass fiber filter and a microporous membrane.

11. The blood filtering unit of claim 6 wherein the blood filtering material consists essentially of a glass fiber filter and a microporous membrane.

12. The blood filter unit of claim 6 wherein the agglutinate checking member has projections extending therefrom.

\* \* \* \* \*